US008585648B2

(12) United States Patent
Caffey

(10) Patent No.: US 8,585,648 B2
(45) Date of Patent: Nov. 19, 2013

(54) CATHETER DRUG PUMP

(75) Inventor: Sean Caffey, Manhattan Beach, CA (US)

(73) Assignee: MiniPumps, LLC, Pasadena, CA (US)

( * ) Notice: Subject to any disclaimer, the term of this patent is extended or adjusted under 35 U.S.C. 154(b) by 0 days.

(21) Appl. No.: 13/186,051

(22) Filed: Jul. 19, 2011

(65) Prior Publication Data
US 2012/0016299 A1    Jan. 19, 2012

Related U.S. Application Data

(60) Provisional application No. 61/365,446, filed on Jul. 19, 2010.

(51) Int. Cl.
*A61M 1/00* (2006.01)

(52) U.S. Cl.
USPC .......................................... 604/151

(58) Field of Classification Search
USPC .................................... 604/151, 153
See application file for complete search history.

(56) References Cited

U.S. PATENT DOCUMENTS

| | | | | |
|---|---|---|---|---|
| 5,993,374 A | * | 11/1999 | Kick | 600/8 |
| 6,852,097 B1 | | 2/2005 | Fulton, III | |
| 7,606,615 B2 | | 10/2009 | Makower et al. | |
| 7,867,203 B2 | | 1/2011 | Rosenberg et al. | |
| 7,931,643 B2 | | 4/2011 | Olsen et al. | |
| 2005/0096707 A1 | | 5/2005 | Hill et al. | |
| 2007/0255233 A1 | | 11/2007 | Haase | |
| 2008/0097412 A1 | | 4/2008 | Shuros et al. | |
| 2008/0243071 A1 | | 10/2008 | Quijano et al. | |
| 2008/0269664 A1 | * | 10/2008 | Trovato et al. | 604/20 |
| 2009/0306585 A1 | * | 12/2009 | Pang et al. | 604/67 |
| 2009/0306594 A1 | | 12/2009 | Pang et al. | |
| 2009/0306595 A1 | * | 12/2009 | Shih et al. | 604/151 |
| 2009/0306633 A1 | * | 12/2009 | Trovato et al. | 604/891.1 |
| 2010/0049120 A1 | * | 2/2010 | Dijksman et al. | 604/66 |

FOREIGN PATENT DOCUMENTS

| | | |
|---|---|---|
| EP | 0815896 | 1/1998 |
| WO | WO-01/026706 | 4/2001 |
| WO | WO-03/072193 | 9/2003 |
| WO | WO-2006/060586 | 6/2006 |
| WO | WO-2007/138590 | 12/2007 |
| WO | WO-2009/137780 | 11/2009 |
| WO | WO-2011/028997 | 3/2011 |

OTHER PUBLICATIONS

International Search Report and Written Opinion mailed Dec. 1, 2011 for International Application No. PCT/US2011/044508 (12 pages).

* cited by examiner

*Primary Examiner* — Aarti B Berdichevsky
(74) *Attorney, Agent, or Firm* — Bingham McCutchen LLP

(57) ABSTRACT

A miniaturized drug pump can actively dispense fluid at a controlled (or controllable) flow rate emerging at or near the distal tip of a catheter.

17 Claims, 4 Drawing Sheets

CATHETER DRUG PUMP

CROSS-REFERENCE TO RELATED APPLICATION

This application claims priority to and the benefit of, and incorporates herein by reference in its entirety, U.S. Provisional Patent Application No. 61/365,446, filed on Jul. 19, 2010.

TECHNICAL FIELD

The invention relates, generally, to internal delivery of pharmaceuticals to patients, and, in particular, to systems and methods for delivery drugs via a catheter.

BACKGROUND

Catheter surgery requires minimally invasive tools for small, remotely operated procedures inside the body. Examples of such surgeries and procedures include delivery of a drug (such as tissue plasminogen activator, or tPa) to an arterial blood clot in order to treat stroke or renal-artery stenosis patients, the release of bioactive agents into the myocardium, release of chemotoxic agents into a tumor, and administration of anti-inflammatory drugs after placing pacemaker or brain leads. Other procedures amenable to catheter surgery include repair of or implantation within the heart, stomach, kidney, pancreas, colon, bowel, brain and other tissues.

Many types of "diagnostic catheters" travel along a guidewire and deliver fluid injected from the catheter's proximal handpiece, which is controlled by the surgeon. The fluid-delivery system typically includes a through-lumen in fluid communication with a passageway integrated with an elongated coil component of the guidewire system for steering. Fluid passing through the lumen enters the guidewire through the handpiece's port outside the body while the fluid typically exits the guidewire fluid-delivery system at a selected delivery location, typically along the coil, which can include at the distal tip of the guidewire. Fluids such as drugs have been delivered through this lumen, but at the cost of wasted drug used to fill the dead space, which can be considerable. Also, it is difficult to deliver precise amounts of medication using conventional catheter controls, posing the risk of overdosing and underdosing. Moreover, some patients are allergic to the fluorescein or radiographically opaque contrast fluid injected into the circulation.

Improvements in imaging resolution and X-ray sensitivity may permit use of less drug or imaging-contrast dye without sacrificing clinical benefit. More patients could therefore potentially benefit (or experience fewer side effects) from percutaneous catheter procedures if less dye could be used. Furthermore, images of higher resolution in the area of interest might be obtained if the drug or dye could be better localized. Therefore, a more precise and localized way to deliver contrast fluids to the patient during catheter surgery would be helpful in conjunction with state-of-the-art imaging systems (such as MRI, CT, OCT, etc.).

Precise, local drug delivery to an internal anatomical site would be beneficial in numerous other applications as well. Drug delivery to an atherosclerotic region, for example, has traditionally been given systemically (e.g., an aspirin that can potentially reduce thrombus formation by inactivation of platelets, anti-cholesterol medication that can reduce lipids in the bloodstream and withdraw cholesterol from atherosclerotic plaques, or chelation therapy that uses anticoagulant drugs and nutrients to dissolve plaques directly). Local drug delivery to the arterial wall has more recently been achieved with paclitaxel-eluting stent systems, for example, that are implanted directly along the arterial intima to prevent or delay re-stenosis. But more general or episodic drug delivery not involving device implantation would help prevent systemic side effects while maximizing dosage at the intended target, and in any case, implantation is not an option for many internal targets.

SUMMARY OF THE INVENTION

The present invention relates to a miniaturized drug pump that can actively dispense fluid at a controlled (or controllable) flow rate emerging at the distal tip of a catheter. Using standard techniques for catheterization (e.g., as in invasive cardiology for balloon angiography), a small pump is provided in-line with the catheter or at its distal end. The pump can be activated by the clinician (either wirelessly or by a wired electrical connection to the pump) in order to dispense a small amount—e.g., 1 nL to 3 mL—of liquid at any time during the catheter procedure. This can be provided in the form of a quick injection or slowly released from the pump during surgery. In some embodiments, the catheter is coupled with or includes a balloon which, when inflated, stops blood flow or participates in standard stenting procedures. In other embodiments, the blood is aspirated downstream from the catheter tip (after the dose has been delivered) in order to minimize systemic exposure for dangerous drugs. In another embodiment, the pump is given a radiopaque signature which is easily identifiable on an X-ray or MRI in order to assist the surgeon in locating the pump within the body.

Clinical applications include treatment of cardiac artery clots, liver cancer (i.e., hepatocellular carcinoma), carotid clots, lung tumors inside the bronchus, pancreatic surgery, renal arterial nerve ablation and thrombus removal around the body. The catheter drug pump may be made using MRI-compatible materials such as gold electrodes. Advantages of various embodiments of the present invention include precise injection of drug or contrast agents into a remote part of the body (brain, coronary vessels, pancreatic vessels, etc.) using the minimally invasive techniques of intravascular catheterization; precision, which is especially advantageous for dangerous drugs that can trigger systemic side effects should excess fluid enter the vasculatory system unintentionally; and the ability to inject fluid into a defined portion of the arterial system using a balloon to temporarily close off a section of an artery in order to permit a catheter drug pump to saturate the volume with drug.

In a first aspect, the invention is directed to a drug-delivery pump system for use in connection with a catheter. The system includes a controllable drug pump dimensioned to fit within and move smoothly through a catheter's lumen, a user-operable controller physically separate from the pump, and means facilitating communication between the controller and the pump (such as, e.g., a wire, or wireless transmission and reception circuitry). The pump has an outlet for facilitating controlled delivery of drug through the outlet in response to the controller. The outlet may be on a front face of the pump. The system may further include a guide catheter dimensioned to fit within the lumen. The drug pump may be affixed to the guide catheter in an in-line configuration or at the end of the guide catheter. The guide catheter may include a balloon for stopping blood flow during drug delivery.

In some embodiments, the pump includes a drug reservoir, an outlet, one or more electrolyte chambers, and an expandable diaphragm that separates the chamber and the reservoir and provides a fluid barrier between them. The pump may include one or more fill ports for providing external access to the reservoir and/or the chamber. The pump may also have outlet ports along its side wall(s). The pump may be in the form of a cartridge removably insertable into a catheter at one end of the catheter.

In another aspect, the invention provides, in various embodiments, a catheter drug-delivery pump system including a catheter, a controllable drug pump integrated with the catheter in an in-line configuration, a user-operable controller physically separate from the pump, and means facilitating communication between the controller and the pump. The pump has an outlet for facilitating controlled delivery of drug outside the catheter in response to the controller. The catheter may include two separated lumens, one in which the pump resides and one dimensioned to accommodate a guidewire. The system may further include a battery and circuitry for operating the pump. The battery and circuitry may be located within the pump, or within the catheter outside the pump. In some embodiments, the system includes one or more sensors (such as, e.g., a flow sensor, time-of-flight sensor, and/or thermal sensor) proximate to the outlet. The sensor(s) may measure environmental conditions such as pH, drug concentration, and pressure.

BRIEF DESCRIPTION OF THE DRAWINGS

The foregoing and the following detailed description of the invention may be more readily understood in conjunction with the drawings, in which.

DETAILED DESCRIPTION

Figure 1:
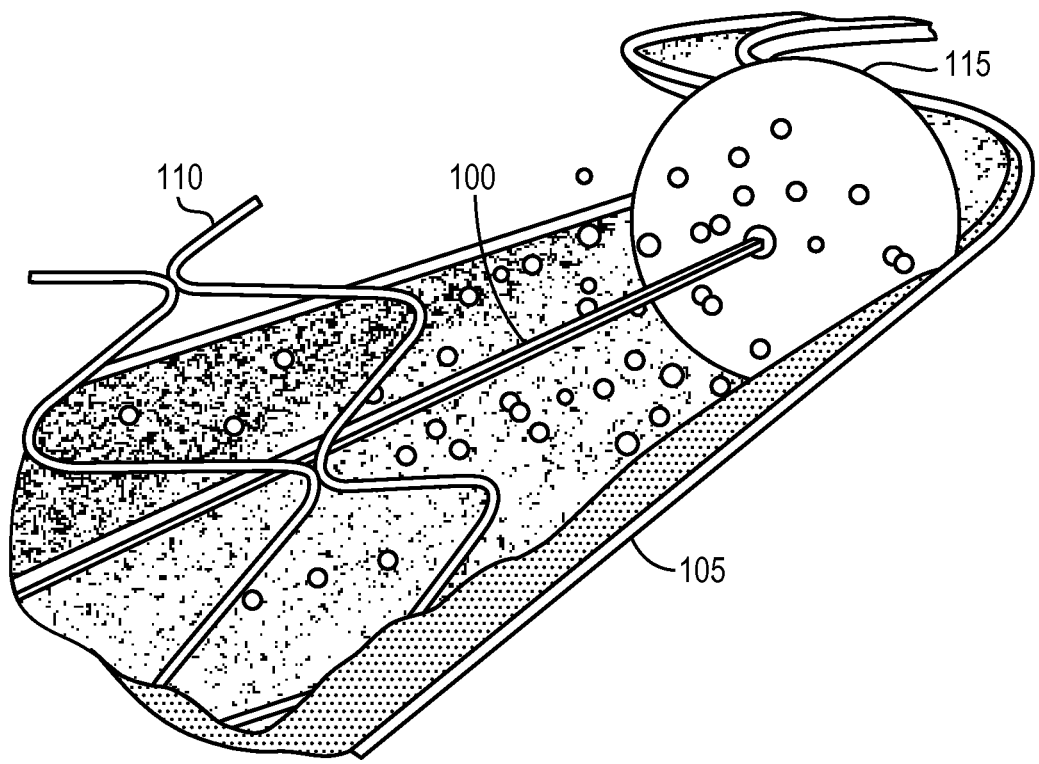
FIG. 1 schematically illustrates a basic catheter configuration in accordance with embodiments hereof.

Refer first to FIG. 1, which illustrates the environment in which a catheter drug pump in accordance with the invention may be deployed. A catheter tube 100 is configured to pass through the interior of a patient's blood vessel 105, which may have therein a stent 110 previously inserted to counteract a localized flow constriction. A balloon 115, positioned at or near the distal end of the catheter tube 100, may be inflated by the clinician in order to block the passage, e.g., to prevent immediate downstream flow of a drug dispensed from the catheter tube 100 upstream of the balloon 115 and localizing the drug's action. Drug flow and balloon inflation can be coordinated in order to provide periodic on and off cycles whereby balloon 115 is rapidly inflated, drug is dispensed, and then balloon 115 deflates a short time later in order to allow blood downstream but not before the drug has had enough time to perfuse the region.

Figure 2:
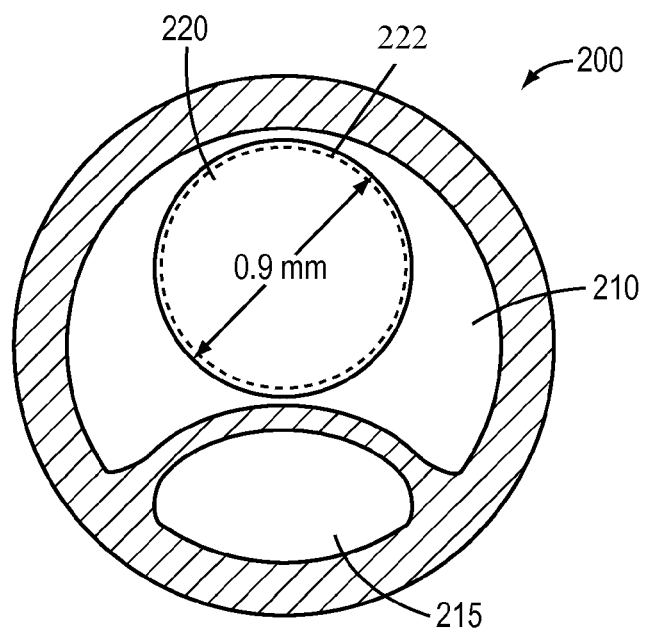
FIG. 2 is a sectional view of a catheter useful in connection with embodiments of the present invention.

A catheter drug pump in accordance herewith may be configured in various ways. FIG. 2 shows a typical catheter 200 in cross-section. The catheter 200 includes two lumens, a working lumen 210 and a guidewire lumen 215. Typically, the lumens 210, 215 are spatially separate and fluidly isolated from each other. A guidewire in lumen 215 allows the clinician, using a conventional hand-held controller, to extend and steer the catheter 200 through body passages such as blood vessels. The guidewire is unspooled from the controller and is stiff enough to push the catheter 200 through body passages but flexible enough to avoid tissue damage. In some embodiments, a drug pump in accordance herewith is permanently integrated within the lumen 210, generally proximal relative to balloon 115; in these embodiments, the lumen 210 may serve as the outer wall of the pump. In other embodiments, the catheter pump is implemented as a cartridge that is mechanically pushed forward inside a catheter with a slightly larger inner diameter to arrive at the proper position within the catheter. In this case, the diameter of the pump is limited by a maximum working diameter 220 within lumen 210, e.g., 0.9 mm in the illustrated embodiment. The cartridge may be constructed from a hard casing (e.g., plastic or metal) in order to facilitate smooth travel down the catheter lumen and to protect the internal pump components. In still another variation, the catheter pump is a distinct unit integrated in an in-line configuration along the length of, or affixed to the tip of, a small-diameter catheter 222 that includes the balloon 115 distal to the drug pump; this smaller catheter 222 is passed through the lumen 210 of a conventional catheter 200 following internal positioning thereof. In these embodiments, in other words, the pump is a segment of the small-diameter catheter 222, and in some embodiments, may be detached for refilling, for example.

Figure 3:
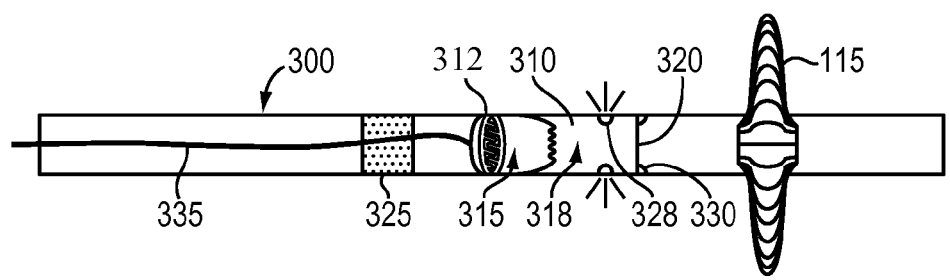
FIG. 3 is a transparent, partially schematic elevation of a drug pump in accordance herewith, deployed in a catheter.

The latter two approaches are illustrated in FIG. 3. Catheters used in angioplasty, for example, have either an "over-the-wire" (OTW) or "rapid exchange" (Rx) design. The illustrated Rx catheter 300 permits a drug pump 310 in cartridge form, or a dedicated pump catheter, to pass through the working lumen. As described in greater detail below, pump 310 includes a series of electrodes 312, an expandable electrolysis chamber 315, and a drug reservoir 318. Determining proper positioning of the pump 310 within the lumen of catheter 300 may be accomplished in various ways. In one embodiment, the pump 310 has an outlet port on its forward face 320, and catheter 300, at least in the region of balloon 115, is porous. The pump 310 is advanced within the catheter 300 until a reference marker (e.g., a radio-opaque marker 325) is cleared, as confirmed by X-ray or other form of external imaging. The pump system can have an imaging signature that identifies it readily on the X-ray. The balloon 115 is inflated and the drug dispensed through the forward port, reaching the body passage through the porous wall of catheter 300. A sensor associated with pump 310 may confirm when a certain volume of the drug has been delivered. Alternatively, the pump 310 may have one or more outlet ports 328 located on, and radially displaced around, the cylindrical wall of drug reservoir 318. In some implementations, the pump cartridge or the small-diameter catheter passes through and partially clears the end of the larger-diameter guiding catheter so that the side outlet ports 328 are exposed to the interior of the body passage, allowing drug to be freely dispensed therein.

In still other implementations, a guiding catheter 300 contains one or more detents 330 or other internal protrusions within the lumen that stop the progress of pump 310 (whether deployed as a cartridge at or near the end of a small-diameter pump catheter, or affixed to the end of the pump catheter) at a position proximate to balloon 115. Detents 330 may also enforce a rotational (circumferential) position of pump 310 within the lumen of catheter 300. With the drug pump 310 rotationally positioned by detents 330, the outlet ports 328 align with complementary apertures through guiding catheter 300 so that drug may be dispensed therethrough.

In various embodiments, the pump has a tether 335 that provides electricity to the internal pump circuitry and electrodes 312, as well as communication therewith and, optionally, feedback from one or more sensors. The tether may also exhibit sufficient mechanical stiffness to push the pump through a catheter into position, but more typically, the pump has a port (as described below) for receiving a guidewire. In some embodiments, the pump has a self-contained power source and bidirectional communication with the pump, as well as provision of sensor signals to the pump circuitry, occur wirelessly, so there is no need for a tether.

Figure 4:
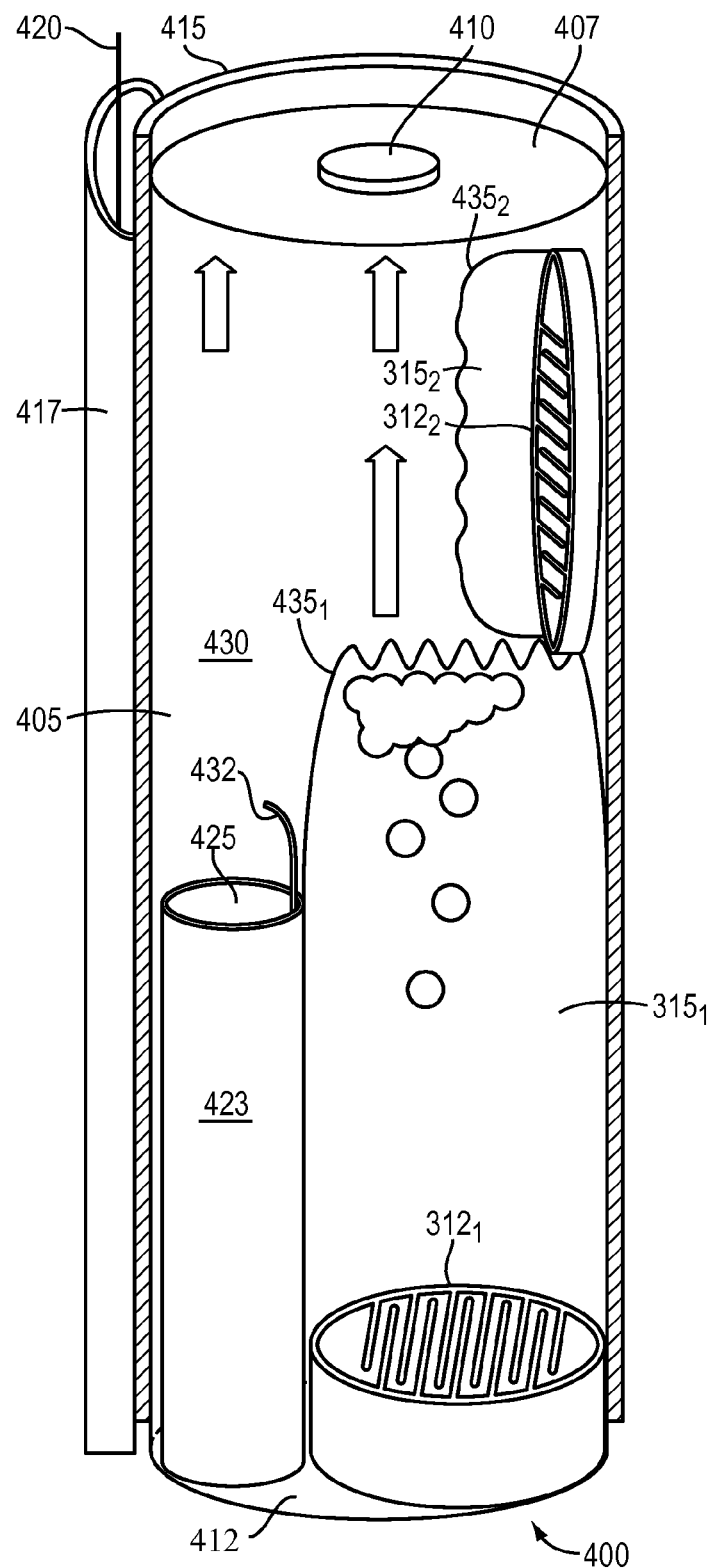
FIG. 4 is a larger transparent, partially schematic elevation of a drug pump in accordance herewith.

In the illustrated embodiment, the pump is an electrolytic pump, as shown in greater detail in FIG. 4. The pump 400 is in the form of a cartridge defined by a cylindrical side wall 405, a front face 407 with an outlet aperture 410 therethrough, and a rear face 412. (As noted above, the outlet port(s) may be located on the side wall 405 rather than on front face 407.) The pump 400 slides smoothly along the interior of a catheter 415, which has a guidewire port 417 in which a guidewire 420 is received. The pump 400 also includes a refill port 423 having an entry point flush with the rear face 412 of pump 400. The entry point and, typically, the body of refill port 423 are made of an elastic biocompatible material such as silicone. The refill port 423 has an open end 425 in fluid communication with the drug reservoir 430. In general, drug reservoir 430 can be refilled by piercing the entry point of refill port 423 with a refill needle (e.g., a standard syringe needle) and driving it into the refill port 423. A hard plastic or metal needle stop 432 prevents the needle from entering the drug reservoir 430 and damaging components therein. In some embodiments, one or more additional refill ports permit replacement of electrolyte solution in the electrolysis chamber 315.

The entry point of refill port 423 is capable of re-sealing itself upon removal of the needle. Moreover, the self-sealing material of the refill port may be able to withstand multiple punctures by the needle. In addition to silicone, materials from which the refill port 423 may be manufactured include, but are not limited to, parylene C, parylene HT, polycarbonates, polyolefins, polyurethanes, copolymers of acrylonitrile, copolymers of polyvinyl chloride, polyamides, polysulphones, polystyrenes, polyvinyl fluorides, polyvinyl alcohols, polyvinyl esters, polyvinyl butyrate, polyvinyl acetate, polyvinylidene chlorides, polyvinylidene fluorides, polyimides, polyisoprene, polyisobutylene, polybutadiene, polyethylene, polyethers, polytetrafluoroethylene, polychloroethers, polymethylmethacrylate, polybutylmethacrylate, polyvinyl acetate, nylons, cellulose, gelatin, and porous rubbers.

To accommodate refill port 423 and other internal components described below, as well as the elongated geometry of drug reservoir 430, a plurality of electrolysis chambers 315 may be employed. Each of the electrolysis chambers $315_1$, $315_2$ has a set of electrodes $312_1$, $312_2$ and an expandable diaphragm $435_1$, $435_2$ (made from, for example, parylene). When the electrode sets $312_1$, $312_2$ are energized to electrolyze an electrolysis fluid (e.g., saline) within the associated chamber $315_1$, $315_2$, evolution of gas expands the diaphragm $435_1$, $435_2$ so that liquid within the drug reservoir 430 is driven out exit port 410 (as indicated by the arrows) at pressures adequate to counter the outer pressure of body fluid. As illustrated, the electrolysis chambers $315_1$, $315_2$ are disposed in perpendicular orientations so that, when with the associated diaphragms $435_1$, $435_2$ expand, they fill most of the interior volume of drug reservoir 430 to maximize the ejection fraction of the drug. Multiple electrolysis chambers also increase the speed of drug ejection. A valve may optionally be associated with port 410 to direct fluid out in one or more outflow streams.

In alternative embodiments, the electrolytic pump may have a piston configuration rather than a diaphragm configuration; that is, evolved gas drives a piston forward rather than expanding a diaphragm to eject drug from the pump. Details of electrolytic pump construction are set forth in U.S. Ser. Nos. 12/463,247, 12/463,265, 12/463,251, all filed on May 8, 2009, and U.S. Ser. No. 13/091,031, filed on Apr. 20, 2011, the entire disclosures of which are hereby incorporated by reference. The capacity and operational lifetime of the drug pump 400 can easily be adjusted by altering the size of the reservoir 430 and the rate at which the drug is administered.

As noted, the electrolysis diaphragms can be formed from parylene; but in addition, the entire housing of pump 400 can also be parylene container since it is biocompatible and compatible with different drugs, having no extractables (i.e., materials that could leach out to harm the drug). The diaphragms, pump housing and cannulas can, for example, be made entirely from a single coating or batch process of parylene.

Optionally, the device's outflow ports (which can be one or more cannulas) can have one or more sensors (such as a flow sensor, time-of-flight sensor, thermal sensor, etc.) associated therewith to measure the flow rate and dose of the fluid delivered, or other parameter indicative of or affecting drug delivery. For example, a flow or pressure sensor placed inside a cannula may be used to measure the drug-delivery rate directly, and feedback circuitry can be employed to adjust the rate of electrolysis in response to sensed variations that deviate from the delivery protocol. The sensors can also be used to measure environmental conditions, such as pH, drug concentration, and pressure at the distal end of the catheter. Multiple pressure sensors may be used to detect a difference in pressure and calculate the flow rate based on a known laminar relationship. For example, a flow sensor (e.g., a MEMS sensor) may be disposed in the outflow cannula to monitor drug flow to the infusion site, and detect potential obstructions in the flow path, variations in drug-pump pressure, etc. The cannula may further include a check valve that prevents backflow of liquid into the drug reservoir 430. In some embodiments, the catheter includes an aspirator for withdrawing delivered drug back into the catheter—e.g., in response to a sensor signal indicating an excessive concentration of drug at the site of administration—or for accelerating the ejected drug downstream through the body passage.

Figure 5A:
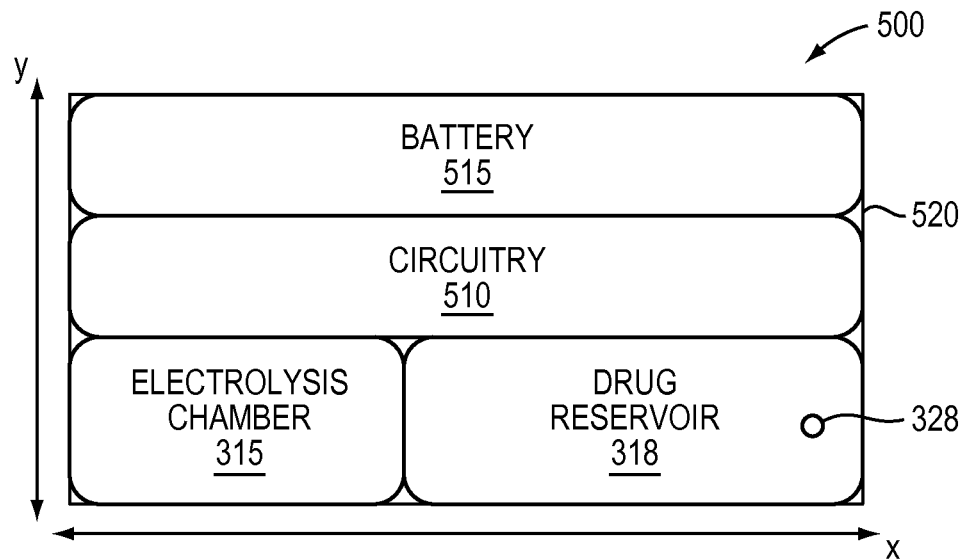
FIGS. 5A and 5B are schematic elevational and end views of a self-powered catheter drug pump in accordance herewith.
Figure 5B:
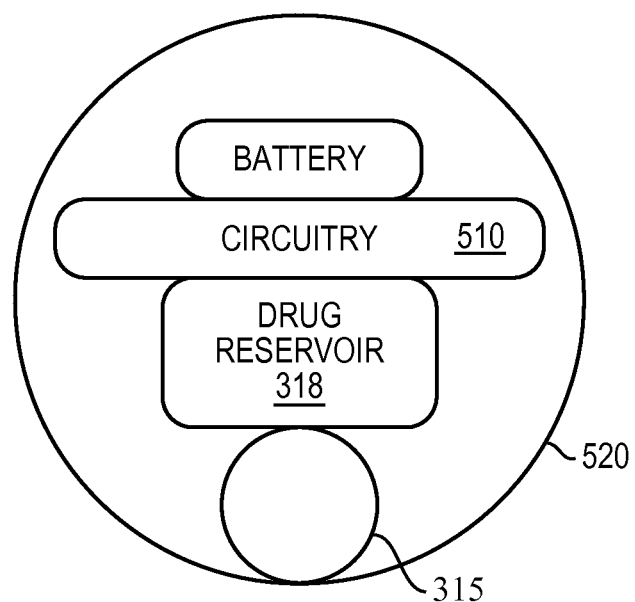

With reference to FIGS. 5A and 5B, a pump 500 with an electrolysis chamber 315 and drug reservoir 318 as described above (and which may be implemented, as noted, in a diaphragm or piston configuration) is operated by electronic circuitry 510, which includes a microcontroller for operating the pump, memory for storing programming for the microcontroller, a wired or wireless telemetry circuit to permit external control, pump actuation, bidirectional communication, and reprogramming, and circuitry for processing sensor signals. The microcontroller is typically an integrated circuit including a processor core, memory (e.g., in the form of flash memory, read-only memory (ROM), and/or random-access memory (RAM)), and input/output ports. The memory may store firmware that directs operation of the drug pump 510. Typically the circuitry is responsive to a wired or wireless signal from the handpiece that operates the catheter guidewire. The clinician may specify a dose and an interval over which the drug is administered, and trigger actuation of the pump 500 when it reaches the appropriate anatomical position or at the proper time during a medical procedure. Alternatively, pump 500 may be controlled and/or re-programmed remotely by a wireless handheld device, such as a customized personal digital assistant (PDA) or a smartphone, i.e., a mobile phone with advanced computing ability that facilitates bi-directional communication and data transfer.

Sensor feedback may be used to compensate for external influences that can affect the infusion rate despite unchanged electrolysis (such as backpressure from the infusion site or cannula clogging). For example, signals from a flow sensor may be integrated to determine when the proper dosage has been administered, at which time the control circuitry terminates the operation of the pump 500. The system controller may also assess the flow through the outlet port or cannula as reported by a flow sensor, and take corrective action if the flow rate deviates sufficiently from a programmed or expected rate. If the control circuitry determines that a higher flow rate of drug is needed, it may increase the current to the electrolysis electrodes to accelerate gas evolution in the electrolysis chamber; conversely, if the control circuitry determines that a lower flow rate of drug is needed, it may decrease the current to the electrolysis electrodes.

The circuitry 510 and electrolysis electrodes may be powered by a battery 515. Suitable batteries 515 include non-rechargeable lithium batteries approximating the size of batteries used in wristwatches, as well as rechargeable Li-ion, lithium polymer, thin-film (e.g., Li-PON), nickel-metal-hydride, and nickel cadmium batteries. In the illustrated embodiment, the battery is co-located with circuitry 510 in the pump housing, and the pump is delivered through a catheter. Alternatively, however, the battery 515 may be located remotely—e.g., within the catheter or the hand-held controller—and wired to the pump via tether 335 (see FIG. 1).

As indicated schematically in FIG. 5A, the various components of the pump device 500 may be housed together a small enclosure 520, measuring, for example, about 2 mm in length x and 0.5 mm in height y. The enclosure 520, whether integrated at the end of a catheter or configured for travel through a catheter lumen, may have a guidewire port to facilitate travel.

A representative procedure for inserting a drug pump implemented, along with a balloon, at the end of a catheter is as follows:
A) Insert guidewire (0.035" diameter) into patient and maneuver to the anatomical point of interest (e.g., coronary artery through the femoral artery);
B) Insert diagnostic catheter by threading the catheter lumen over the guidewire until the tip is in the desired location;
C) Remove guidewire;
D) Introduce fluid (such as imaging contrast dye) down catheter (e.g., to image blocked coronary vessels);
E) Insert guiding catheter;
F) Replace guiding catheter with 0.014" wire; and
G) Advance pump catheter along wire until destination reached.

A representative application for a catheter drug pump involves thrombolysis. Many strategies have been developed to prevent atherosclerotic deposits from forming in patients who are prone to them (due to high cholesterol, hypertension, or enhanced systemic susceptibility to blood clots), but limited options exist for breaking up clots once they form. Several thrombolytic agents have been developed to reduce clots, and these are especially desirable for stroke and heart-attack patients. Three groups of thrombolytic agents are generally available: enzymes, which act directly upon the fibrin strands within the clot; plasma activator agents, which increase plasma activator activity; and plasminogen activators, such as streptokinase, urokinase, and tissue plasminogen. All of these drugs increase the amount of plasmin (which dissolves clots) in the blood.

tPA is currently the most popular and expensive drug for thrombolysis. It activates only fibrin-bound plasminogen and thus targets the clot site. tPA is typically given in intravenous solution, but delivery from a catheter pump in accordance herewith offers various advantages, including cost reduction (tPA is very expensive drug, so filling a diagnostic catheter's dead space in order to achieve local delivery is wasteful); minimizing systemic exposure to tPA (which can dissolve clots and potentially save lives, but can also cause a stroke if given to the wrong patient or for the wrong type of condition); and maximizing the local effect of tPA on the clot.

Mechanical thrombolytic procedures such as balloon angioplasty are also in common use, but a disadvantage of these procedures is that not all of the clot is removed. When the balloon is inflated, it expands the stent and opens up the diseased segment into a rounder, larger and smoother opening compared to angioplasty. Accordingly, stents tend to induce a more predictable and satisfactory result. Unfortunately, the material within the expanded channel starts to expand within a few days, and while drug-coated stents can help prevent the re-stenosis, they cannot remove the plaque. For example, in balloon thrombectomy, only enough clot is extracted and aspirated in order to allow the balloon to force the clots into the intimal side walls (which restores blood flow but leaves the thrombus to grow again or possibly embolize). Therefore, combining the localized perfusion of drugs with mechanical aspiration of the clot (with a suction tube or a balloon filter) using embodiments of the present invention can remove more of the clot. In addition, the drug can include agents for preventing re-stenosis.

Another application of catheter drug pumps in accordance herewith involves localized treatment of tissue disorders. The oral bioavailability of some drugs may be low due to poor absorption from the gastrointestinal tract. Such drugs may require administration in very high doses or by a combination of routes such as injection directly to the bloodstream, the muscle and/or a diseased tissue (e.g., a tumor). For drugs that exhibit rapid onset, or that trigger severe side effects, large systemic injections may not be suitable. For example, salbutamol, used to treat pulmonary conditions, can affect the heart and circulation if taken orally; these effects are greatly reduced by inhaling smaller doses directly into the lungs. An artery leading to a pancreatic tumor may be treated locally with a chemotoxic agent, e.g., in combination with surgical extraction. More generally, a drug or dye may provide improvements to healing or extraction outcomes or better visualization.

Another application of catheter drug pumps in accordance herewith involves convection-enhanced delivery (CED), or the continuous injection under positive pressure of a fluid containing a therapeutic agent directly into tissue. Placing the catheter drug pump through a hole in the skull, for example, and navigating the tip to the site of interest inside the brain parenchyma has the advantage of bypassing the blood-brain barrier. A drug pump can store the volume of therapeutic fluid in an optimal location along the catheter depending on the application—e.g., a proximal location since backflow can occur from catheters that are larger in its distal portion. A catheter drug pump for CED has the advantages of minimizing backflow and decreasing the pressure sink that can occur between the tissue the distal tip of the catheter by placing the pump flush with the tissue; pressure feedback can be used to modulate the flow, and this arrangement facilitates consistent application the proper flow into the tissue, preventing edema that can result from high volumes of fluid not reaching the target (e.g., drug infusion into white matter can cause edema while in grey matter it occurs less). Furthermore, a prefilled drug pump can avoid bubbles entering the parenchyma, a condition that can make the delivery of the drug highly variable and which is often encountered when fluids are delivered by a traditional catheter.

Another application of catheter drug pumps in accordance herewith involves infusion of very small amounts of fluid that can be dangerous to the rest of the body (e.g., NOS gene transfection or adenovirus transfection of VEGF to ischemic illiac arteries), or radioactive materials that need to be shielded by the drug pump and infused directly into the artery or vein.

Drugs such as an anti-arrhythmia agent may be injected into the coronary vessels, e.g., in the right coronary artery, which supplies the SA node region. This can be useful in treating primary arrhythmias, or secondary or iatrogenic arrhythmias caused during surgery. Amiodarone is an anti-arrhythmic agent used to treat various types of tachyarrhythmias (fast forms of irregular heart beat), including both ventricular and supra-ventricular (atrial) arrhythmias. One mL infused directly into the right coronary artery using a catheter drug pump may have a direct effect on returning the heart back to a normal sinus rhythm quickly. This administration can be combined with an intravenous loading dose (typically 300 mg in 20-30 cc D5W for cardiac arrest, or 150 mg in a 100 cc bag of D5W given over 10 minutes for dysrhythmias), but the catheter-supplied dose can direct the drug quickly to the site of action.

Having described certain embodiments of the invention, it will be apparent to those of ordinary skill in the art that other embodiments incorporating the concepts disclosed herein may be used without departing from the spirit and scope of the invention. For example, various features described with respect to one particular device type and configuration may be implemented in other types of device and alternative device configurations as well. Accordingly, the described embodiments are to be considered in all respects as only illustrative and not restrictive.

What is claimed is:

1. A drug-delivery pump system for use in connection with a catheter, the system comprising:
   a controllable drug pump;
   a guide catheter to which the drug pump is fixedly retained in an in-line configuration, the guide catheter being dimensioned to fit within a lumen of the catheter;
   a user-operable controller physically separate from the pump; and
   means facilitating communication between the controller and the pump, the pump having an outlet for facilitating controlled delivery of drug therethrough in response to the controller.

2. The system of claim 1, wherein the guide catheter has an end to which the drug pump is affixed.

3. The system of claim 1, wherein the guide catheter further comprises a balloon for stopping blood flow during drug delivery.

4. The system of claim 1 wherein the pump has outlet ports along a side wall thereof.

5. The system of claim 1 wherein the outlet is on a front face of the pump.

6. The system of claim 1 wherein the communication-facilitating means comprises a wire.

7. The system of claim 1 wherein the communication-facilitating means comprises wireless transmission and reception circuitry.

8. The system of claim 1 wherein the pump comprises:
   a drug reservoir;
   an outlet;
   an electrolyte chamber; and
   an expandable diaphragm separating the chamber and the reservoir and providing a fluid barrier therebetween.

9. The system of claim 8 wherein the pump comprises at least one fill port for providing external access to at least one of the reservoir or the chamber.

10. The system of claim 8 further comprising at least one additional electrolyte chamber.

11. A catheter drug-delivery pump system comprising:
    a catheter;
    a controllable drug pump integrated and fixedly retained therewithin in an in-line configuration;
    a user-operable controller physically separate from the pump; and
    means facilitating communication between the controller and the pump, the pump having an outlet for facilitating controlled delivery of drug outside the catheter in response to the controller.

12. The system of claim 11 further comprising a battery and circuitry for operating the pump, the battery and circuitry being located within the pump.

13. The system of claim 11 further comprising a battery and circuitry for operating the pump, the battery and circuitry being located within the catheter and not within the pump.

14. The system of claim 11 wherein the catheter comprises first and second fluidly separated lumens, the pump residing in the first lumen and the second lumen being dimensioned to accommodate a guidewire.

15. The system of claim 11 further comprising one or more sensors proximate to the outlet.

16. The system of claim 15 wherein the one or more sensors comprise at least one of a flow sensor, a time-of-flight sensor, or thermal sensor.

17. The system of claim 15 wherein the one or more sensors measure at least one environmental conditions selected from pH, drug concentration, and pressure.

* * * * *